United States Patent
Nucci et al.

(10) Patent No.: US 9,949,910 B2
(45) Date of Patent: Apr. 24, 2018

(54) CLEANSING COMPOSITIONS AND METHODS OF USE THEREOF

(71) Applicant: INNOSPEC LIMITED, Ellesmere Port (GB)

(72) Inventors: John Nucci, Salisbury, NC (US); Stephen Moss O'Connor, Charlotte, NC (US)

(73) Assignee: INNOSPEC LIMITED, Cheshire (GB)

( * ) Notice: Subject to any disclaimer, the term of this patent is extended or adjusted under 35 U.S.C. 154(b) by 0 days.

(21) Appl. No.: 14/366,848

(22) PCT Filed: Dec. 20, 2012

(86) PCT No.: PCT/GB2012/053205
§ 371 (c)(1),
(2) Date: Jun. 19, 2014

(87) PCT Pub. No.: WO2013/093473
PCT Pub. Date: Jun. 27, 2013

(65) Prior Publication Data
US 2014/0342974 A1 Nov. 20, 2014

Related U.S. Application Data

(60) Provisional application No. 61/579,075, filed on Dec. 22, 2011.

(51) Int. Cl.
| | |
|---|---|
| *A61K 8/46* | (2006.01) |
| *C11D 1/12* | (2006.01) |
| *C11D 17/00* | (2006.01) |
| *A61Q 19/10* | (2006.01) |

(52) U.S. Cl.
CPC .............. *A61K 8/466* (2013.01); *A61Q 19/10* (2013.01); *C11D 1/126* (2013.01); *C11D 17/006* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 2,894,912 A | 7/1959 | Geitz | |
| 2008/0058237 A1* | 3/2008 | Brennan et al. | 510/153 |
| 2012/0295987 A1* | 11/2012 | Misner et al. | 514/770 |

FOREIGN PATENT DOCUMENTS

| | | |
|---|---|---|
| GB | 954833 A | 4/1964 |
| WO | 94/09763 A1 | 5/1994 |
| WO | 2005075623 A1 | 8/2005 |
| WO | 2007/130390 A2 | 11/2007 |

OTHER PUBLICATIONS

International Search Report for International Application No. PCT/GB2012/053205 dated Apr. 19, 2013.
Gough, T. "Sulfate-Free Made Easy: Rationale and Guide to Formulating Highly Appealing Sulfate-Free Personal Care Compositions." Copyright Innospec, Ltd. (Jun. 6, 2012), retrieved from www.in-cosmetics.com.
Wortzman et al. "Soap and detergent bar rinsability" (1986) J. Soc. Cosmet. Chem. 37:89-97.

* cited by examiner

*Primary Examiner* — Necholus Ogden, Jr.
(74) *Attorney, Agent, or Firm* — Burns & Levinson LLP; Janine M. Susan

(57) ABSTRACT

A method of improving the rinsability of a cleansing composition comprising an isethionate ester surfactant of formula $R^6COOCH_2CH_2SO_3^-M^+$ the method comprising incorporating into the composition one or more compounds of formula (I) wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and M+ represents a cation.

(I)

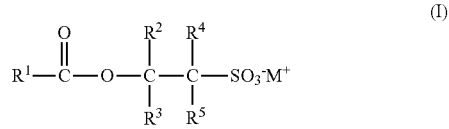

17 Claims, No Drawings

CLEANSING COMPOSITIONS AND METHODS OF USE THEREOF

CROSS-REFERENCE TO RELATED APPLICATIONS

This application is a U.S. national stage application under 35 U.S.C. 371 of co-pending International Application No. PCT/GB2012/053205, filed on Dec. 20, 2012, and entitled METHODS AND COMPOSITIONS, which in turn claims benefit of and priority to U.S. Provisional Patent Application No. 61/579,075, filed on Dec. 22, 2011, which is incorporated by reference herein in its entirety for all purposes.

The present invention relates to cleansing compositions comprising isethionate ester surfactants. In particular the invention relates to solid cleansing compositions comprising these surfactants.

The use of isethionate ester surfactants in cleansing compositions is well known. These compounds, including sodium lauroyl isethionate and sodium cocoyl isethionate, have been found to be mild to the skin and provide good lathering. They have been used in cleansing compositions in addition to or in place of soap. They are used in particular in beauty bars.

These may contain only the isethionate synthetic detergent or they may be combination beauty bars comprising synthetic detergent and soap.

Although synthetic detergents based on isethionate esters are advantageous in terms of their mildness to the skin and good foaming properties they suffer from some disadvantages. One of these is that beauty bars comprising high levels of synthetic detergent wear much more quickly than traditional soap bars and produce high levels of mush. A further disadvantage is that users have complained that cleansing compositions comprising these type of surfactants leave a residue on the skin and can cause a slimy feel. Increased rinsing is therefore needed following the use of such compositions compared to when using traditional soap. The problem of poor rinsability increases as higher levels of the isethionate esters are incorporated into a cleansing composition.

It is an object of the present invention to provide an improved cleansing composition.

According to a first aspect of the present invention there is provided a method of improving the rinsability of a cleansing composition comprising an isethionate ester surfactant of formula $R^6COOCH_2CH_2SO_3^-M^+$, the method comprising incorporating into the composition one or more compounds of formula (I):

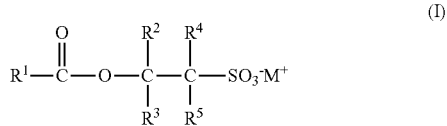

wherein $R^1$ and $R^6$ each independently represents a $C_{4-36}$ substituted or unsubstituted hydrocarbyl group;

each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen; and $M^+$ represents a cation.

The present invention relates to a method of improving the rinsability of a cleansing composition. By rinsability we mean to refer to the ease with which a composition can be washed away from the skin or other surface to which it is applied. A composition having an improved rinsability will leave a lower residue on the skin or other surface after use compared with a composition having a poorer rinsability. Users report a cleaner skin feel following use of a composition having improved rinsability.

The present invention relates to a method of improving the rinsability of a cleansing composition. Preferably the composition is a solid cleansing composition, for example a bar or block composition having the general appearance of a bar of soap. These are known in the art as beauty bars.

The cleansing compositions used in the present invention comprise isethionate ester surfactants of formula $R^6COOCH_2CH_2SO_3^-M^+$. The skilled person will appreciate that the compounds of formula (I) are also isethionate esters. For the avoidance of doubt in this specification references to isethionate esters relate to compounds of formula $R^6COOCH_2CH_2SO_3^-M^+$ and compounds of formula (I) will be referred to as alkyl isethionate esters.

$R^6$ is preferably a substituted or unsubstituted alkyl or alkenyl group. Preferably $R^6$ is an unsubstituted alkyl or alkenyl group, most preferably an unsubstituted alkyl group. Preferably $R^6$ represents a C5 to C30 alkyl group, preferably a C7 to C24 alkyl group, more preferably a C7 to C21 alkyl group, most preferably a C7 to C17 alkyl group.

$M^+$ preferably represents an optionally substituted ammonium cation or more preferably a metal cation. Suitable ammonium cations include $NH_4^+$ and the ammonium cation of triethanolamine. Preferred metal cations are monovalent metal cations, for example sodium, lithium and potassium cations; and divalent metal cations for example zinc, calcium and magnesium cations. Preferably $M^+$ is a zinc, sodium or potassium cation. Most preferably $M^+$ is a sodium cation.

The skilled person will appreciate that when $M^+$ is a divalent metal cation two moles of anion will be present for each mole of cation.

In especially preferred embodiments the isethionate ester surfactant present in the cleansing composition is selected from sodium lauroyl isethionate, sodium cocoyl isethionate and mixtures thereof.

The cleansing composition preferably comprises at least 10 wt % isethionate ester surfactant of formula $R^6COOCH_2CH_2SO_3^-M^+$ preferably at least 20 wt %, more preferably at least 25 wt %, suitably at least 27 wt %, preferably at least 30%. Preferably the isethionate ester surfactant is present in an amount of at least 32 wt %, more preferably at least 35 wt %.

The isethionate ester surfactant of formula $R^6COOCH_2CH_2SO_3^-M^+$ may be present in the composition in an amount of up to 90 wt %, preferably up to 80 wt %, more preferably up to 75 wt %, suitably up to 70 wt %, preferably up to 67 wt %, preferably up to 65 wt %, more preferably up to 63 wt %, for example up to 60 wt %.

The above amounts refer to the percentage by weight of isethionate surfactant of formula $R^6COOCH_2CH_2SO_3^-M^+$ compared to the total amount of all ingredients present in the composition.

The composition may comprise a mixture of two or more isethionate ester compounds of formula $R^6COOCH_2CH_2SO_3^-M^+$. In such embodiments the above amounts refer to the total amount of all such compounds present in the composition.

In this specification unless otherwise stated all amounts refer to the actual amount of active compound present in the composition. The skilled person will appreciate that commercial sources of isethionate esters and alkyl isethionate esters may contain side products and impurities. However amounts referred to in this specification unless otherwise stated refer to the amount of active ingredient present and do not include any impurity, side product or diluent that may be present.

The method of the present invention may be useful in improving the rinsability of a cleansing composition comprising isethionate ester surfactants and which is substantially free from traditional soap components. However it is particularly useful for improving the rinsability of cleansing compositions comprising a mixture of isethionate ester surfactants and soap.

In some preferred embodiments the cleansing composition comprises at least 1 wt % or at least 3 wt % soap, preferably at least 5 wt % soap, for example at least 7 wt % soap, suitably at least 8 wt % soap, for example at least 10 wt % soap.

The composition may comprise up to 40 wt % soap, suitably up to 35 wt % soap, preferably up 30 wt % soap, suitably up to 25 wt % soap preferably up to 22 wt % soap, for example up to 20 wt % soap.

The above amounts refer to the percentage by weight of soap compared to the total amount of all ingredients present in the composition.

In this specification any reference to soap, traditional soap or soap component refers to compounds that are commonly known as soaps, i.e. salts of fatty acids.

A soap component may include the alkali metal or alkanol ammonium salts of aliphatic alkane or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. Soaps useful herein may include the well known alkali metal salts of natural of synthetic aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are C16 and higher. Preferred soaps for use in the present invention have at least about 85% fatty acids having about 12 to 18 carbon atoms.

Coconut oil employed for the soap component may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap component is a mixture of about 15% to about 20% coconut oil and about 80% to about 85% tallow. These mixtures contain about 95% fatty acids having about 12 to about 18 carbon atoms. The soap component may be prepared from coconut oil, in which case the fatty acid content is about 85% of C12-C18 chain length.

The soaps may contain unsaturation in accordance with commercially acceptable standards. Excessive unsaturation is normally avoided.

Beauty bars can be prepared comprising any ratio of isethionate ester surfactant to soap. The present invention finds particular utility in cleansing compositions comprising from 30 to 70 wt %, especially 35 to 60 wt % isethionate ester surfactant of formula $R^6COOCH_2CH_2SO_3^-M^+$ and 5 to 40 wt %, especially 10 to 30 wt % soap.

The ratio of soap to isethionate ester surfactant may suitably be selected to balance the requirements of mildness to the skin and prevention of wear or mushiness.

The method of the present invention involves incorporating into the composition one or more compounds of formula (I):

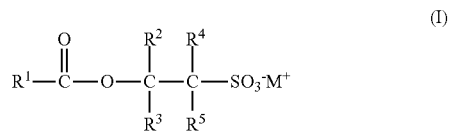

Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group.

Preferably $R^1$ represents a $C_{5-30}$ alkyl group, preferably a $C_{7-24}$ alkyl group, more preferably a $C_{7-21}$ alkyl group, most preferably a $C_{7-17}$ alkyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the present invention may include a mixture of more than one compound of formula (I). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is is alkyl (suitably methyl) and $R^2$, $R^3$ and $R^4$ are all hydrogen.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a zinc, potassium or sodium cation. Most preferably $M^+$ represents a sodium cation.

The skilled person will appreciate that when $M^+$ is a divalent metal cation two moles of anion will be present for each mole of cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably methyl.

In preferred embodiments the one or more compounds of formula (I) is the reaction product of sodium methyl isethionate and a fatty acid, that is a compound of formula $R^1COOCHR^2CHR^4SO_3^-M^+$ in which one of $R^2$ and $R^4$ is methyl and the other is hydrogen.

In especially preferred embodiments the composition comprises a mixture of isomers, that is a compound of formula $R^1COOCH_2CHR^4SO_3^-M^+$ in which $R^4$ is alkyl (preferably methyl) and a compound of formula $R^1COOCHR^2CH_2SO_3^-M^+$ in which $R^2$ is alkyl (preferably methyl).

In some embodiments the composition of the present invention comprises one or more of sodium lauroyl methyl isethionate, sodium cocoyl methyl isethionate and sodium oleoyl methyl isethionate.

Most preferably the composition of the present invention comprises sodium lauroyl methyl isethionate and/or sodium cocoyl methyl isethionate. Sodium lauroyl methyl isethionate is especially preferred.

The compound of formula (I) is preferably present in an amount of at least 0.5 wt % based on the amount of isethionate ester surfactant in the composition. Preferably it is present in an amount of at least 1 wt % based on the amount of isethionate ester surfactant, preferably at least 2 wt %, more preferably at least 3 wt %, preferably at least 4 wt %, for example at least 5 wt %.

Suitably the compound of formula (I) is present in an amount of up to 40 wt % based on the amount of isethionate ester surfactant in the composition. Preferably it is present in an amount of up to 35 wt % based on the amount of isethionate ester surfactant in the composition, more preferably up to 30 wt %, suitably up to 25 wt %, for example up to 23 wt %, preferably up to 22 wt %, for example up to 20 wt %.

Suitably the compound of formula (I) is present in an amount of at least 0.1 wt % based on the total weight of the cleansing composition, preferably at least 0.5 wt %, more preferably at least 0.75 wt %, preferably at least 1 wt %, suitably at least 1.25 wt %, preferably at least 1.5 wt %. It may be present in an amount of at least 2 wt %, at least 3 wt % or at least 4 wt %.

Suitably the compound of formula (I) is present in an amount of up to 30 wt % based on the total weight of the cleansing composition, preferably up to 25 wt %, more preferably up to 20 wt %, preferably up to 18 wt %, suitably up to 15 wt %, preferably up to 13 wt %. It may be present in an amount of up to 12 wt %, up to 10 wt % or up to 9.5 wt %.

The composition may comprise a mixture of two or more compounds of formula (I). In such embodiments the above amounts refer to the total amount of all such compounds present in the composition.

According to a second aspect of the present invention there is provided a cleansing composition comprising from 30 to 70 wt % isethionate ester surfactant of formula $R^6COOCH_2CH_2SO_3^-M^+$; from 5 to 40 wt % soap; and from 1 to 35 wt % based on the weight of the isethionate ester surfactant of one or more compounds of formula (I):

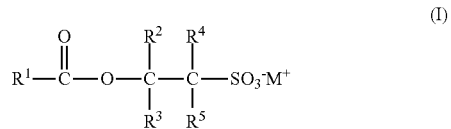

wherein $R^1$ and $R^6$ each independently represents a $C_{4-36}$ substituted or unsubstituted hydrocarbyl group;

each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen; and $M^+$ represents a cation.

Where appropriate features of the first aspect may apply to the compositions of the second aspect.

Preferred features of the second aspect defined herein may apply to the cleansing compositions described in the first aspect.

The composition of the present invention is preferably a solid composition. Preferably it is in the form of a beauty bar. The composition preferably has acceptable wear properties, provides good foaming and does not form excessive mush.

Suitably the isethionate ester surfactant, the soap and the compound of formula (I) together comprise at least 36 wt % of the composition, suitably at least 40 wt %, preferably at least 50 wt %, more preferably at least 60 wt %. Suitably these components together comprise from 60 to 80 wt % of the total composition.

The composition of the present invention may comprise a chelating agent. Suitable chelating agents include ethylenediamine-N,N'-disuccinic acid, methylglycinediacetic acid, glutamic acid N,N-diacetic acid, imino disuccinic acid, diethylene triamine pentaacetic acid, ethylenediamine tetraacetic acid, diethylenetriamine penta methylene phosphonic acid, etidronic acid and anions and mixtures thereof.

Preferred chelants are biodegradable chelants for example ethylenediamine-N,N'-disuccinic acid, methylglycinediacetic acid, glutamic acid N,N-diacetic acid, imino disuccinic acid and anions and mixtures thereof.

Suitably the composition comprises from 0.1 to 5 wt %, suitably from 0.5 to 2 wt % of a chelating agent. One especially preferred chelating agent is trisodium ethylenediamine disuccinate.

Other components which may be present in the cleansing composition are those typically found in such compositions, epecially beauty bar compositions and will be known to the person skilled in the art. Further optional ingredients include for example fragrances, dyes, structuring aids, fillers pH adjustment agents, chelating agents and conditioning agents.

Suitable further ingredients for use in beauty bars include structuring aids or fillers which can be used to improve the processing properties of the bar mixture, to enhance the prepared bar integrity and enhance desired user sensory profiles. Components of this type include fatty acids; salts of fatty acids; polyalkylene glycols and derivatives; starches and dextrins, maltodextrin and other carbohydrates; inorganic particulate materials for example talc, kaolin, bentonite clay, aluminosilicate clays or other clays; carbonate or sulphate salts; glycerol esters or ethylene glycol esters; sugars and crystalline polyols; other waxes and fatty alcohols.

Other additives which may be included in the cleansing composition include fragrances or perfumes; germicides; antimicrobial agents; antioxidants; cationic polymers; and sequestering agents for example sodium ethylenediaminetetraacetate (EDTA) and trisodium ethylenediamine disuccinate (EDDS). The composition may include ingredients used to enhance appearance for example pigments, colorants and dyes; opacifiers and pearlizers for example titanium dioxide, zinc stearate or magnesium stearate. The cleansing composition may include emollients for example benzoate esters or additional mild surfactants. Surfactants may be selected from anionic, cationic or amphoteric surfactants and include for example, betaines, taurates, alkyl ether carboxylates, acyl glutamates, acyl sarcosinates, alkyl sulfates and alkyl ether sulfates. The composition may also include additional water.

Suitably the composition may comprise one or more fatty acids. These may be present in an amount of 1 to 40 wt %, suitably from 5 to 35 wt %, for example from 10 to 30 wt %, or from 20 to 30 wt %. Any suitable fatty acids can be used and will be known to the person skilled in the art. Preferred fatty acids include stearic acid and coconut fatty acid.

The composition may suitably comprise a betaine surfactant. One suitable example is cocoamidopropyl betaine. This may be present in an amount of up to 5 wt %, for example from 0.5 to 2.5 wt %.

In some embodiments the composition may contain sodium isethionate. This may be present in an amount of up to 5 wt %, for example from 0.5 to 2.5 wt %.

Preferably the cleansing compositions of the present invention have a pH of between 4 and 10, suitably they have a pH of between 5 and 9, preferably they have a pH of between 6 and 9.5. Most preferably they have a pH of between 6.5 and 8.

According to a third aspect of the present invention there is provided the use of one or more compounds of formula (I):

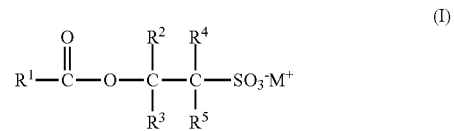

wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; to improve the rinsability of a cleansing composition comprising an isethionate ester surfactant of formula $R^6COOCH_2CH_2SO_3^-M^+$ wherein $R^6$ represents a $C_{4-36}$ substituted or unsubstituted hydrocarbyl group.

Preferred features of the third aspect are as defined in relation to the first and second aspects.

According a fourth aspect of the present invention there is provided a method of cleansing the skin, the method comprising the steps of:

(i) contacting the skin with a composition comprising an isethionate ester surfactant of formula $R^6COOCH_2CH_2SO_3^-M^+$ and one or more compounds of formula (I):

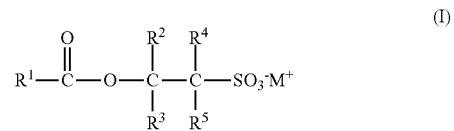

wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and (ii) rinsing the composition from the skin with water.

Suitably in step (ii) less water is needed to rinse the composition from the surface than would be needed if an otherwise equivalent cleansing composition was used which did not contain a compound of formula (I).

Suitably following step (ii) a lower amount of residue remains on the skin than would be present if an otherwise equivalent cleansing composition was used which did not contain a compound of formula (I).

Preferably following the rinsing step (ii) substantially all of the composition has been removed from the skin.

Preferably following the cleansing method of the fourth aspect skin feels clean and fresh and there is no feeling of residue remaining on the skin.

Preferred features of the fourth aspect are as defined in relation to the first and second aspects. In a particularly preferred embodiment of the fourth aspect step (i) comprises contacting human skin with a composition of the second aspect.

According to a fifth aspect of the present invention there is provided a method of manufacturing a cleansing composition having improved rinsability, the method comprising admixing an isethionate ester surfactant of formula $R^6COOCH_2CH_2SO_3^-M^+$, one or more compounds of formula (I):

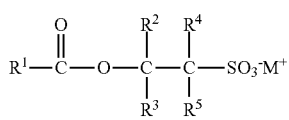

(I)

wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and optionally soap and further ingredients.

Preferably the method of the fifth aspect involves admixing solid components and compacting to form a bar. Any suitable method may be used. Standard techniques for producing beauty bars will be known to the person skilled in the art. One preferred method involves extrusion and stamping.

The invention will now be further described with reference to the following non-limiting examples.

EXAMPLE

Beauty bars were prepared comprising the following ingredients:

TABLE 1

| | A (comparative) | B (comparative) | C (invention) | D (invention) |
|---|---|---|---|---|
| Pureact I78/80 (wt %) | | 75.8 | 56.7 | 61 |
| Iselux (RTM) (wt %) | | | 16.0 | 12 |
| Soap A (wt %) | 100 | 10 | 10.0 | 20 |
| Stearic acid (wt %) | | 11.7 | 14.8 | 5 |
| Water (wt %) | | 2.5 | 2.5 | 2 |

Pureact I-78/80 is a commercially available composition containing 63-68 wt % sodium cocoyl isethionate and approximately 35 wt % fatty acids (coconut fatty acid and stearic acid).

Iselux® is a commercially available composition comprising at least 80 wt % of sodium lauroyl methyl isethionate and a maximum of 7 wt % lauric acid.

Soap A is a commercially available soap mixture comprising about 78 wt % of an 85/15 blend of sodium tallowate/cocoate, about 7 wt % glycerine, 13 wt % water, 1.4 wt % fatty acid and 0.5 wt % sodium chloride The water included was deionized and filtered.

The bars were produced via by extrusion process. The compositions were prepared by adding the components in the order listed in table 1 and mixing in a Mazzoni laboratory amalgamator. After mixing for 10 minutes, the base composition was transferred to the hopper of a Mazzoni laboratory plodder and refined through a screen. This step was repeated and upon completion the material was again placed in to the hopper of the laboratory plodder fitted with a conical extrusion head and die plate. The composition was extruded into a bar billet and cut into slugs approximately the length of the final bar form. The slugs were stamped into their final form using an air-driven Mazzoni semi-automatic soap press.

Bars A, B, C and D were tested as follows. In addition, a 100% soap bar referred to as a Standard Soap bar was used in this test to 'condition' the skin before and between testing of experimental samples.

The inner aspect of the forearm was washed with the Standard Soap Bar. This preliminary wash was performed in a standard manner under running tap water at 30° C. for 30 seconds. Tap water was delivered at the rate of about 300 mL every 5 seconds. The skin was lightly patted dry with a paper towel and then dried with a hair dryer (medium setting) for 1 minute to remove superficial moisture from the skin surface. Immediately after drying the washed area of the forearm was placed on the diamond cell of an FTIR spectrometer. (The warm up and background scans were completed in advance.) The infrared spectrum was recorded in the range from 4000 to 400 $cm^{-1}$ to provide a baseline reading. In these experiments the spectrometer used was a Varian 1000 FT-IR spectrometer equipped with a Diamond ATR cell such as the Pike GladiATR.

The same area of skin was used to test compositions A, B, C and D under the same conditions of tap water flow rate and temperature. The area to be tested (approximately 70 square centimeters) was held under running tap water for 10 seconds. The test bar was wetted and using the edge of the bar the skin was stroked for 20 cycles covering the entire test area. One cycle was one back and forth stroke. The composition was not rinsed from the skin. After air drying for 30 seconds the area was lightly patted with a paper towel to remove some of the excess water, taking care not to wipe any of the composition from the skin. The area was then dried using a hair dryer for 1 minute. The infrared spectrum was measured in the same way as described previously to give the "dried on" reading.

The test area was held under running tap water (30° C., 300 mL/5 seconds) for 5 seconds. It was allowed to dry for 30 seconds and then patted lightly with a paper towel, before drying using a hair dryer on medium setting for 1 minute. The FTIR spectrum was again recorded to give the "rinsed" reading.

By overlaying the IR spectra it was possible to determine if any residue remained on the skin surface after rinse off. Qualitative or semi-quantitative analysis was achieved by measuring the transmittance of the reference peaks which are characteristic of the compositions applied and well resolved from those of the baseline reading.

In the case of composition A identification peaks could be seen in the infrared spectrum at approximately 1400 $cm^{-1}$ and 1560 $cm^{-1}$. For compositions B, C and D identification peaks could be seen at approximately 1060 $cm^{-1}$ and 1180 $cm^{-1}$.

Table 2 compares the peaks at 1560 $cm^{-1}$ (composition A) and 1180 $cm^{-1}$ (compositions B, C and D).

| | % transmission of identification peak | | |
|---|---|---|---|
| | Prior to applying composition | After applying composition | After rinsing |
| Composition A | 0 | 3.9 | 0 |
| Composition B | 0 | 26 | 7.5 |
| Composition C | 0 | 22 | 0 |
| Composition D | 0 | 24 | 1.5 |

With compositions A and C the user reported that the composition had rinsed clean from the skin. With composition B the user reported a feeling of a residue remaining on the skin. No comment was recorded for composition D.

The invention claimed is:

1. A method of improving the rinsability of a cleansing composition comprising an isethionate ester surfactant of formula $R^6COOCH_2CH_2SO_3^-M^+$ and soap, the method comprising:
improving the rinsability of the cleansing composition by: incorporating into the composition 0.1 to 20 wt % based on total weight of the composition of one or more compounds of formula (I):

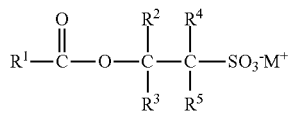

wherein $R^1$ and $R^6$ each independently represents a $C_{4-36}$ substituted or unsubstituted hydrocarbyl group;
each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation;
wherein the isethionate ester surfactant, the soap and the compound of formula (I) together comprise at least 50 wt %;
and wherein the cleansing composition is a solid composition.

2. The method according to claim 1 wherein the isethionate ester surfactant is selected from sodium lauroyl isethionate, sodium cocoyl isethionate or mixtures thereof.

3. The method according to claim 1 wherein the compound of formula (I) is selected from sodium lauroyl methyl isethionate, sodium cocoyl methyl isethionate, sodium oleoyl methyl isethionate and mixtures thereof.

4. The method according to claim 1 wherein the one or more compounds of formula (I) comprise a mixture of isomers including a compound of formula $R^1COOCH_2CHR^4SO_3^-M^+$ in which $R^4$ is $C_1$ to $C_4$ alkyl and a compound of formula $R^1COOCHR^2CH_2SO_3^-M^+$ in which $R^2$ is $C_1$ to $C_4$ alkyl.

5. A solid cleansing composition comprising from 30 to 70 wt % isethionate ester surfactant of formula $R^6COOCH_2CH_2SO_3^-M^+$, from 5 to 40 wt % soap and from 1 to 35 wt % based on the weight of the isethionate ester surfactant of one or more compounds of formula (I):

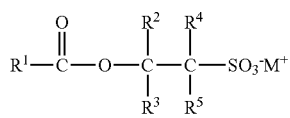

wherein $R^1$ and $R^6$ each independently represents a $C_{4-36}$ substituted or unsubstituted hydrocarbyl group;
each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation.

6. The cleansing composition according to claim 5 which further includes one or more ingredients selected from fragrances, dyes, structuring aids, fillers, pH adjustment agents, chelating agents and conditioning agents.

7. A method of cleansing the skin, the method comprising the steps of:
(i) contacting the skin with a solid cleansing composition comprising an isethionate ester surfactant of formula $R^6COOCH_2CH_2SO_3^-M^+$, soap and 0.1 to 20 wt % based on total weight of the composition of one or more compounds of formula (I):

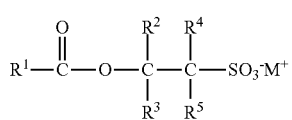

wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; wherein the isethionate ester surfactant, the soap and the compound of formula (I) together comprise at least 50 wt %; and
(ii) rinsing the composition from the skin with water.

8. The method according to claim 7 wherein in step (ii) less water is needed to rinse the composition from the surface than would be needed if an otherwise equivalent cleansing composition was used which did not contain a compound of formula (I).

9. A method of manufacturing the cleansing composition according to claim 5, the method comprising admixing an isethionate ester surfactant of formula $R^6COOCH_2CH_2SO_3^-M^+$, 0.1 to 20 wt % based on total weight of the composition of one or more compounds of formula (I):

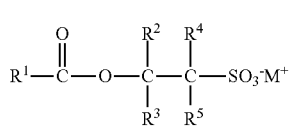

wherein $R^1$ and $R^6$ each independently represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; soap and optionally further ingredients.

10. A method of improving the rinsability of a cleansing composition comprising an isethionate ester surfactant of formula $R^6COOCH_2CH_2SO_3^-M^+$ and soap, the method comprising:
improving the rinsability of the cleansing composition by: incorporating into the composition 0.1 to 9.5 wt % based on total weight of the composition of one or more compounds of formula (I):

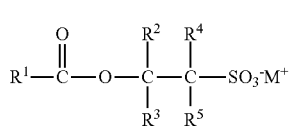

wherein $R^1$ and $R^6$ each independently represents a $C_{4-36}$ substituted or unsubstituted hydrocarbyl group;

each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation;

wherein the isethionate ester surfactant, the soap and the compound of formula (I) together comprise at least 50 wt %;

and wherein the cleansing composition is a solid composition.

11. The method according to claim 10 wherein the isethionate ester surfactant is selected from sodium lauroyl isethionate, sodium cocoyl isethionate or mixtures thereof.

12. The method according to claim 10 wherein the compound of formula (I) is selected from the group consisting of sodium lauroyl methyl isethionate, sodium cocoyl methyl isethionate, sodium oleoyl methyl isethionate and mixtures thereof.

13. The method according to claim 10 wherein the one or more compounds of formula (I) comprise a mixture of isomers including a compound of formula $R^1COOCH_2CHR^4SO_3^-M^+$ in which $R^4$ is $C_1$ to $C_4$ alkyl and a compound of formula $R^1COOCHR^2CH_2SO_3^-M^+$ in which $R^2$ is $C_1$ to $C_4$ alkyl.

14. A method of improving the rinsability of a cleansing composition comprising an isethionate ester surfactant of formula $R^6COOCH_2CH_2SO_3^-M^+$ and soap, the method comprising:

improving the rinsability of the cleansing composition by: incorporating into the composition 0.1 to 20 wt % based on total weight of the composition of one or more compounds of formula (I):

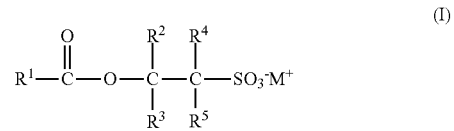

wherein $R^1$ and $R^6$ each independently represents a $C_{4-36}$ substituted or unsubstituted hydrocarbyl group;

each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation;

wherein the isethionate ester surfactant is present in an amount of 10 to 60 wt % and the isethionate ester surfactant, the soap and the compound of formula (I) together comprise at least 50 wt %;

and wherein the cleansing composition is a solid composition.

15. The method according to claim 14 wherein the isethionate ester surfactant is selected from sodium lauroyl isethionate, sodium cocoyl isethionate or mixtures thereof.

16. The method according to claim 14 wherein the compound of formula (I) is selected from the group consisting of sodium lauroyl methyl isethionate, sodium cocoyl methyl isethionate, sodium oleoyl methyl isethionate and mixtures thereof.

17. The method according to claim 14 wherein the one or more compounds of formula (I) comprise a mixture of isomers including a compound of formula $R^1COOCH_2CHR^4SO_3^-M^+$ in which $R^4$ is $C_1$ to $C_4$ alkyl and a compound of formula $R^1COOCHR^2CH_2SO_3^-M^+$ in which $R^2$ is $C_1$ to $C_4$ alkyl.

* * * * *